US006872292B2

(12) United States Patent
Theeuwes et al.

(10) Patent No.: US 6,872,292 B2
(45) Date of Patent: Mar. 29, 2005

(54) VOLTAGE MODULATION OF ADVANCED ELECTROCHEMICAL DELIVERY SYSTEM

(75) Inventors: Felix Theeuwes, Los Altos, CA (US); Jeremy Corwin Wright, Los Altos, CA (US)

(73) Assignee: Microlin, L.C., Salt Lake City, UT (US)

( * ) Notice: Subject to any disclaimer, the term of this patent is extended or adjusted under 35 U.S.C. 154(b) by 20 days.

(21) Appl. No.: 10/353,770

(22) Filed: Jan. 28, 2003

(65) Prior Publication Data

US 2004/0144646 A1 Jul. 29, 2004

(51) Int. Cl.[7] .............................. B01D 61/44; A61N 1/30
(52) U.S. Cl. ........................ 204/520; 204/630; 604/20
(58) Field of Search ................................ 204/520, 630; 604/20

(56) References Cited

U.S. PATENT DOCUMENTS 4,886,514 A * 12/1989 Maget ..................... 604/891.1
6,289,241 B1 * 9/2001 Phipps ......................... 604/20

* cited by examiner

Primary Examiner—Arun S. Phasge
(74) Attorney, Agent, or Firm—Factor & Lake

(57) ABSTRACT

An electro-osmotic cell capable of substantially reducing zero-current transport is disclosed, wherein the cell includes a cell housing having a first half cell and a second half cell, with an ion selective membrane therebetween, a first electrode positioned within the first half cell, a second electrode positioned within the second half cell, an electrolyte in electrical communication with the first electrode and the second electrode, and a wiring apparatus electrically connecting the first electrode and the second electrode, wherein the wiring apparatus has one or more structures used for counteracting salt concentration increases within the electro-osmotic cell. Such a cell may be used within an electro-osmotic fluid delivery device, along with a fluid inlet, a piston member adjacent the electro osmotic cell, and a drug reservoir adjacent the piston member, wherein the drug reservoir includes a sealed compartment having an exit port. A method for using such a device is similarly disclosed.

57 Claims, 2 Drawing Sheets

VOLTAGE MODULATION OF ADVANCED ELECTROCHEMICAL DELIVERY SYSTEM

BACKGROUND OF THE INVENTION

1. Field of the Invention

The present invention is drawn generally to electrochemical fluid delivery devices, and specifically to an improved electro-osmotic fluid delivery system.

2. State of the Prior Art

Fluid delivery devices are well known in the art, ranging from pressurized fluid delivery, to mechanical fluid delivery, to electrochemical fluid delivery devices and beyond. One particularly interesting fluid delivery system is an electro-osmotic cell coupled with a delivery pump, forming an electro-osmotic pump. These simple pumps operate through the combination of an electrochemical cell and an ion-selective membrane to create a driving force for fluid delivery.

Conventional electro-osmotic pumps, however, have a number of problems that have not, as of yet, been addressed in the prior art. One particular problem has occurred in constant fluid delivery applications. As the operation of the device is continued over a period of time, it has been observed that the delivery rate is inconsistent, even though the current rate between the anode and the cathode is maintained at a constant rate. Generally, two types of osmosis are occurring with an electro-osmotic cell simultaneously. The primary and most prevalent type of osmosis is electro-osmosis, whereby charged ions (salts) are driven across an ion exchange membrane as the cell is operated, thereby dragging water molecules along its path. The secondary, and less prevalent form of transport is osmosis due to environmental conditions. Osmosis is the transfer of a solvent across a barrier, generally from an area of lesser solute concentration to an area of greater concentration. Given normal cell operating conditions, the environmentally-driven osmosis is negligible in comparison to the electro-osmosis.

As the relative concentrations of salts within the half cells of an electro-osmotic delivery device change, however, significant changes in the amount of fluid delivered have been observed. It has been postulated that as operation of the device is continued, the passage of ions (salts) across the membrane of the device causes an increase in the salt concentration within one of the half-cells resulting in an increased osmotic flow of a solvent across the membrane. Thus, environmental osmosis becomes more prevalent, and affects the predictability and reliability of the cell operations. The fluid transfer causes an increase in the overall fluid amount contained in the one half-cell, increasing the rate of delivery of fluid.

The above-described effect can continue even after the operation of current within the cell has stopped. Even though the anode and the cathode are removed from electrical communication with one another, the concentration difference between the half-cells remains. Thus, additional electrolyte/solvent will continue to be transported across the membrane, causing the fluid delivery device to continue delivering fluid even after the cell has ceased operation. This additional fluid delivery is termed "zero-current transport," and is deemed unacceptable—especially for long term use of a constant-rate fluid delivery device.

It is a thus an object of the present invention to eliminate, or substantially reduce, unwanted zero-current transfer.

It is another object of the present invention to provide an improved cell design wherein the concentration differences between the half-cells within the device are mitigated or avoided.

It is another object of the present invention to increase the reliability and consistency of the delivery rate of the device.

These and other objects will become apparent to one of ordinary skill in the art in light of the present specification, claims and drawings appended hereto.

SUMMARY OF THE INVENTION

Figure 1:
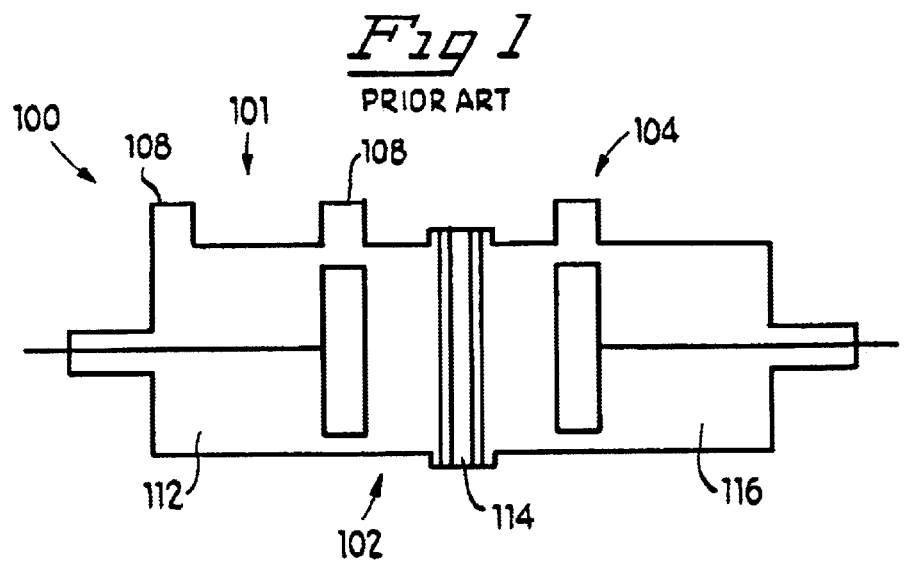
FIG. 1 of the drawings depicts a cut-away side view of prior-art electrochemical fluid delivery device.

The present invention, disclosed herein, teaches an electro-osmotic cell having an improved mechanism for the cessation of cell operations after removal of operational current. The electro-osmotic cell includes a cell housing with a first half cell and a second half cell, which are separated by an ion-exchange membrane. Within each half cell is an electrode; a first electrode within the first half cell, and a second electrode within the second half cell. The electro-osmotic cell also includes an electrolyte in electrical communication with the first electrode and the second electrode, a wiring apparatus electrically connecting the first electrode and the second electrode. All of these elements ensure the normal operation of the electro-osmotic cell. Additionally, however, the electro-osmotic cell includes means for counteracting at least some of the effects of salt concentration increases within the electro-osmotic cell associated with the wiring apparatus. The counteracting means ensures that, after operation of the cell has been halted, the zero-current transport seen in conventional electro-osmotic cells can be minimized.

Preferably, the electrolyte used within the electro-osmotic cell can be any solution containing $Na^+$ and/or $K^+$ and $Cl^-$ ions, such as fluid from a body (where the solvent is water and the electrolytes are naturally-occurring salt ions such as sodium and chloride ions) that can be delivered from the surrounding tissues to an implanted fluid delivery device. Alternatively, a number of other electrochemically compatible bodily fluids could similarly be used (e.g., Ringer's solution, renal dialysis solution, PBS etc).

In a preferred embodiment of the invention, the wiring apparatus of the electro-osmotic cell includes a forward wiring loop and a reverse wiring loop. In this embodiment, both of the forward wiring loop and the reverse wiring loop have a switch for enabling the electrical connection the loops. Specifically, the switch associated with the forward wiring loop can be closed so as to allow current to flow from the first electrode to the second electrode. Alternatively, a switch associated with the reverse wiring loop can be closed so as to allow current to flow from the second electrode to the first electrode. In order to further facilitate current flow in the reverse wiring loop, the counteracting means of the electro-osmotic cell comprises a power source associated with the reverse wiring loop, helping to drive current within that wiring loop. Additionally, it is preferred that the reverse wiring loop includes a controlling element capable of controlling the magnitude and/or time course of current flow across that loop.

In another preferred embodiment, the first and second electrodes of the electro-osmotic cell include both a forward and a reverse electrode. The forward electrodes of both the first electrode and the second electrode are connected through the forward wiring loop. Similarly, the reverse electrodes of the first and second electrodes are connected through the reverse wiring loop. Thus, in this embodiment, the forward loop and reverse loop can comprise separate wiring structures.

Further, the electro-osmotic cell of this embodiment may include a sensing means for detecting a parameter such as the concentration of at least one ionic species within the first and/or second half cells. The sensing means can detect the concentration by, for example, detecting the conductivity within the first and/or second half cells or detecting the electrode potential of the second electrode. The sensing means may comprise a separate sensor or may comprise a sensing circuit connecting the forward second electrode and the reverse second electrode, between the forward first electrode and the reverse first electrode, or between the forward first electrode and the forward second electrode, as may be needed.

Preferably, the first electrode is an anode, the second electrode is a cathode, and the membrane is cationic selective membrane. Alternatively, the first electrode could be a cathode, the second electrode an anode, and the membrane is anionic selective membrane. Anode materials may be of any suitable material to which a cation will migrate in a given electrolytic reaction, and may include materials such as carbon, platinum, zinc, magnesium, manganese, aluminum, silver, and silver/silver chloride. Cathode materials can include carbon, platinum, zinc, magnesium, manganese, aluminum, silver, and silver/silver chloride, among others. As with the dual-electrode embodiment, a single first electrode and a single second electrode preferably include a sensing means for detecting ionic concentration within the cell.

Such an electro-osmotic cell can beneficially be utilized within an electro-osmotic fluid delivery device. The above-described cell, along with all of the preferred embodiments of that cell, can deliver fluid by combining the cell with a fluid inlet, a movable barrier such as a piston member adjacent the electro osmotic cell, and a drug reservoir adjacent the piston member/movable barrier, the drug reservoir comprising a sealed compartment having an exit port. Preferably, the fluid inlet comprises a membrane (such as a permeable membrane or osmotic membrane), or a fluid conduit. Also, the piston member/movable barrier preferably comprises a slideable piston, or a flexible diaphragm.

Such a device can be beneficially used in a method for controlling the unwanted fluid flow out of the electro-osmotic delivery device. The method preferably includes the steps of (1) delivering a fluid using an electro-osmotic fluid delivery device having an electro-osmotic cell therein, wherein the step of delivering the fluid causes an increase in a salt concentration within the electro-osmotic cell, (2) sensing the salt concentration within the electro-osmotic cell, (3) halting the step of delivering, and (4) counteracting the increased salt concentration by reversing the direction of current proportionally (either as a linearly or some more complex proportional relationship) to the sensed salt concentration so as to reduce unwanted zero current transport, and, in turn, unwanted fluid delivery out of the fluid delivery device. Preferably, the step of sensing comprises the step of sensing the conductivity differences between at least two of a forward first electrode, a forward second electrode, a reverse first electrode and a reverse second electrode, wherein the forward and reverse first electrodes are located within a first half cell of the electro-osmotic cell, and the forward and reverse second electrodes are located within a second half cell of the electro-osmotic cell.

In yet another embodiment of this invention, the electro-osmotic cell contains forward first and second electrodes and controlling circuitry connecting the electrodes. A coulometric circuit element is contained within the controlling circuitry. The salt increase in the half cell will be a function of the charge passed. To halt delivery, the current is reversed for a time and magnitude based on the charge passed, as sensed by the coulometric element. This embodiment may include reverse first and second electrodes. The coulometric element may be complex and able to sense both forward and reverse currents, with the controlling element using these data in a complex manner to apply the reverse current.

DETAILED DESCRIPTION OF THE INVENTION

While this invention is susceptible of embodiment in many different forms, there is shown in the drawings and will be described in detail, several specific embodiments with the understanding that the present disclosure is to be considered as an exemplification of the principles of the invention and is not intended to limit the invention to the embodiments illustrated.

A prior art electrochemical device 100 comprising an electro-osmotic pump is shown in FIG. 1 as including fluid inlet 101, electro-osmotic (or electrochemical) cell 102, and fluid outlet 104. The fluid inlet 101 is shown as a pair of fluid conduits 108, which provide and then return a fresh supply of saline to cell 102, as needed. The electro-osmotic cell 102 is typically made up of a first half-cell 112, membrane 114, and second half-cell 116. Conventional devices such as the one shown in FIG. 1 typically operate by introducing a fluid into first half-cell 112, and pumping a portion of the fluid through membrane 114 by the electrochemical transfer of an ion across membrane 114. The fluid introduced into second half-cell 116 accumulates, delivering a fluid contained within second half cell 116 out of cell 102 via fluid outlet 104.

Typically, such prior art electro-osmotic devices, which may be used in fluid delivery systems, have a number of drawbacks. Although such devices are effective in delivering fluid through electro-osmotic transport, the consistency and predictability of fluid delivery can be affected through osmotic transport during and after cessation of the operation of the device. During operation of the cell, conventional cells see an increase in the salt concentration within the cell itself. The salt concentration increase can affect cell operations, and, in particular, acts as a driving force for unwanted osmotic transport within the cell. This effect can even extend beyond cessation of electro-osmotic transport, causing osmotic transport even after cell current has been cut off. This type of post-operational osmotic transport is termed zero-current transport.

Figure 2:
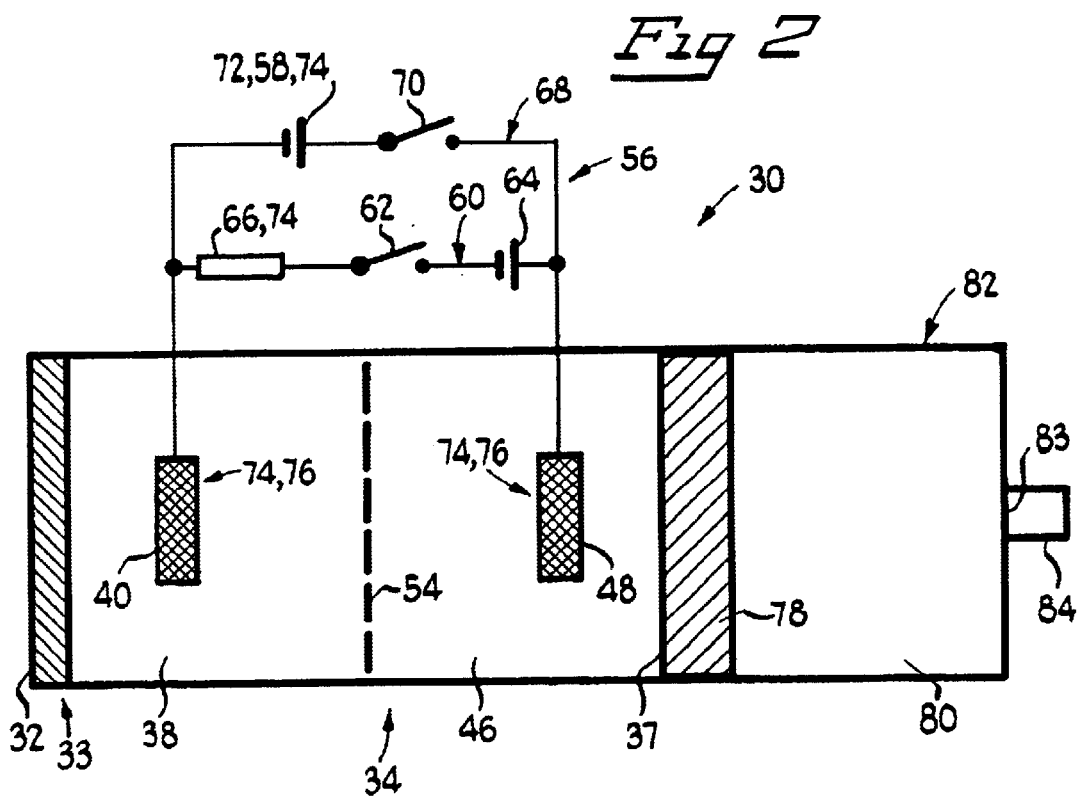
FIG. 2 of the drawings shows a cut-away side view of the fluid delivery device of the present invention.

Fluid delivery device 30 of the present invention helps to overcome these problems, among others. Fluid delivery device 30 of the present invention is shown in FIG. 2 as generally comprising an elongated cylindrical shaped device. The teachings of the present invention may be utilized with a wide variety of fluid-delivery devices. One particularly useful application for the present pump technology is in implantable medical pumps. These pumps are implanted within patients for the delivery of medicament to a patient over a long period of time. The teachings of the present invention will be discussed relative to such an implantable device, and will be shown within such an environment. Although device 30 is shown in conjunction with the implantable devices, it should be noted that the teachings contained within this specification and the appended claims may be translated to other devices and applications without straying from the intended scope of this disclosure.

Fluid inlet 32 of fluid delivery device 30 is shown in FIG. 2 as generally comprising a porous, permeable or semiperiable membrane associated with an end portion 33 of fluid delivery device 30. Preferably, fluid delivery device 30 is associated with a water-rich environment, such as being implanted in a human body, so that, during operation, water may be allowed into cell 34 through inlet 32. Alternatively, and as shown in FIG. 1, fluid inlet 32 could comprise one or more conduits for the delivery of a fluid into cell 34. In any case, the fluid inlet of the particular device should provide a constant and ready supply of fluid for the electro-osmotic cell so as to ensure ongoing and consistent operation.

Electro-osmotic cell 34 is shown in FIG. 2 as comprising first half-cell 38 and second half-cell 46, with ion-selective membrane 54 in-between. Fluid inlet 32 is shown associated with first half-cell 38, allowing fluid from the surrounding environment of fluid delivery device 30 into cell 34. Within first half-cell 38 and second half-cell 46 are electrodes, shown in FIG. 3 with first electrode 40 in first half-cell 38, and second electrode 48 in second half-cell 46. As will be described further in the operation section below, first electrode 40 and second electrode 48 comprise an anode and a cathode electrode, respectively. Alternatively, first electrode 40 could comprise a cathode, and second electrode 48 could comprise an anode, depending upon the materials selected for the electrodes and membrane 54, and the operation of the fluid delivery device 30. Thus, these electrodes are interchangeable within first half-cell 38 and second half-cell 46 of cell 34, depending upon the particular materials used for first electrode 40 and second electrode 48 and for membrane 54.

Numerous materials can be used for both first electrode 40 and second electrode 48, but they must be electrochemically compatible with one another so as to allow for the flow of ions and electrons during cell operation. Typical electrode material pairings could include, among others, Zn/Ag/AgCl, Pt/Pt, Ag/AgCl/Pt, Zn/Pt, Pt/Ag/AgCl, Ag/AgCl/Ag/AgCl, and Zn/AgCl. In one preferred embodiment, first electrode 40 comprises a zinc electrode, and second electrode 48 comprises an Ag/AgCl electrode.

Membrane 54 of cell 34 generally comprises an ion-selective or ion-exchange membrane that allows the passage of the ions, while substantially maintaining the integrity between first half-cell 38 and second half-cell 46. The particular material selected for membrane 54 is dictated by the electrode materials selected and the desired pumping rate of fluid delivery device 30. Typical materials, however, include NAFION, CMI 7000, Membranes International C/R, CMB and CCG-F from Ameridia, AM-1, AM-3 and AM-X from Ameridia and PC-200D from PCA GmBH.

The teachings associated with the electro-osmotic cell 30 of the present device do not necessarily need to be limited to fluid-delivery devices. Applications for the extended use and consistent operation of the cell 34 of the present invention can extend beyond the fluid delivery art, to and including controlled release of any substance in manner that is minimally affected by temperature or pressure. Thus, although the present disclosure is shown in conjunction with a fluid-delivery device, it may be possible to transplant the teachings of the electrochemical cell into another device, as mentioned above, without departing from the scope of this disclosure.

Piston 78 is associated with the distal end 37 of second half-cell 46, sealing off that portion of fluid delivery device 30 from drug reservoir 80. Piston 78 is slideably associated within fluid delivery device 30 so that, as the volume of fluid contained within second half-cell 46 increases or decreases, piston 78 is correspondingly maneuvered into and out of drug reservoir 80. From this process, fluid contained within drug reservoir 80 can be pushed out for delivery, or drawn in if fluid delivery device 30 operations so dictate. Other structures could similarly be utilized to perform the same functional task with an alternative structure. For example, piston 78 could comprise a diaphragm, movable partition, or another similar structure that is capable of conveying an increase in pressure from one compartment to another, while maintaining the integrity of each compartment.

Drug reservoir 80 is shown generally in FIG. 2 as an enclosed portion of fluid delivery device 30 associated with exit port 84 leading out of reservoir 80. Drug reservoir 80 preferably includes a sealed compartment 82. Sealed compartment 82 provides a secure containment system for a drug or other fluid to be enclosed within reservoir 80. Sealed compartment 82 must have at least one opening 83, so as to allow fluid flow out of sealed compartment 82, through exit port 84, and into the surrounding environment.

Exit port 84 preferably comprises an open aperture between the reservoir 80 and the surrounding environment. Although not shown, exit port 84 may additionally include any number of fluid-delivery control devices such as nozzles, valves, or other control devices for regulating flow rate of fluid out of fluid delivery device 30. In its simplest and most preferred form, however, exit port 84 is merely a static aperture, and delivery rate of fluid out of reservoir 80 is dictated entirely by operation of electro-osmotic cell 34.

Wiring apparatus 56 is shown in FIG. 2 as comprising forward wiring loop 60, reverse wiring loop 68, and zero-current transport control means 58, which together help to control the direction and rate of ion flow across membrane 54 to, in turn, control the flow of fluid out of fluid delivery device 30. Forward wiring loop 60 and reverse wiring loop 68 provide an electrical connection between first electrode 40 and second electrode 48 that, in combination with the electrolyte contained in first half cell and second half cell, completes an electrical loop between the electrodes, and across the membrane 54, enabling operation of the electro-osmotic cell 34. Thus, conventional wiring materials can be utilized for both loops. Forward wiring loop 60 and reverse wiring loop 68 can comprise a single electrical wiring connection, or, as shown in FIG. 2, single connections to both the first electrode 40 and second electrode 48, with two separate wiring connections, one comprising the forward wiring loop 60 and one comprising the reverse wiring loop 68.

In order to facilitate normal cell operation, forward wiring loop 60 additionally comprises switch 62, and may additionally include power source 64. When switch 62 is closed, power source 64 provides the potential energy necessary to drive the ions produced by first electrode 40 out of first half-cell 38, through membrane 54, and into second half-cell 46 and second electrode 48. Alternatively, power source 64 could be omitted, and the electrochemical potential of the cell itself would then drive the operation of the system. Further, forward wiring loop 60 may additionally comprise a control element 66, wherein control element 66 provides a regulating mechanism for the flow of current across forward wiring loop 60 that is able to control at least one of the magnitude and time course of current flow. Control element 66 can comprise any number of conventional current controls, including simple mechanisms such as resistors, and more complicated devices such as microprocessor-controlled current controls. Forward wiring loop 60 is utilized during the normal operations of the cell 34.

Reverse wiring loop 68 comprises a similar structure as forward wiring loop 60. Reverse wiring loop 68 is shown in FIG. 2 as having switch 70, and control element 72 (shown as a battery). Similar to the forward wiring loop 60, when switch 70 is closed, reverse wiring loop 68 allows the flow of current from the second electrode 48 out of second half-cell 46, across membrane 54 and into first half-cell 38 and to first electrode 40. Control element 72 again provides regulation for the magnitude and/or the time course of current flow. Additionally, as may be needed, reverse wiring loop 68 can additionally include a power source (if control element 72 isn't itself a power source) for contribution to the potential driving force of current across reverse wiring loop 68. Reverse wiring loop 68, as will be described below, is utilized during the concentration counteracting operation of the cell 34.

Control member 66 or control member 72 may additionally include sensing means 74. Sensing means 74 helps to monitor the build-up of ions within second half-cell 46 as operation of the fluid delivery device 30 commences. Sensing means 74 preferably comprises a sensing circuit 76 connecting first electrode 40 and second electrode 48, which helps to measure the ionic buildup within the second half-cell 46, and could additionally comprise a stand-alone sensor. For example, sensing circuit 76 could measure the difference in concentration measurements of a particular species, or could measure the difference in ionic conductivity between first half cell 38 and second half-cell 46. Similarly, sensing circuit 76 could measure the concentration of a particular species, or the ionic conductivity of a particular half-cell, and utilize a computing element (not shown) and known variables to calculate the differences in ionic conductivity/concentration between the half-cells. In order to do so, sensing circuit 76 comprises any number of conventional ionic sensors or species-specific analyte sensors, such as sodium ion sensor, Ag/AgCl chloride ion sensor, electric conductivity meter etc. Once determined, control member 66 or control member 72 can utilize this information to alter the magnitude/time course of current to properly operate fluid delivery device 30.

Figure 3:
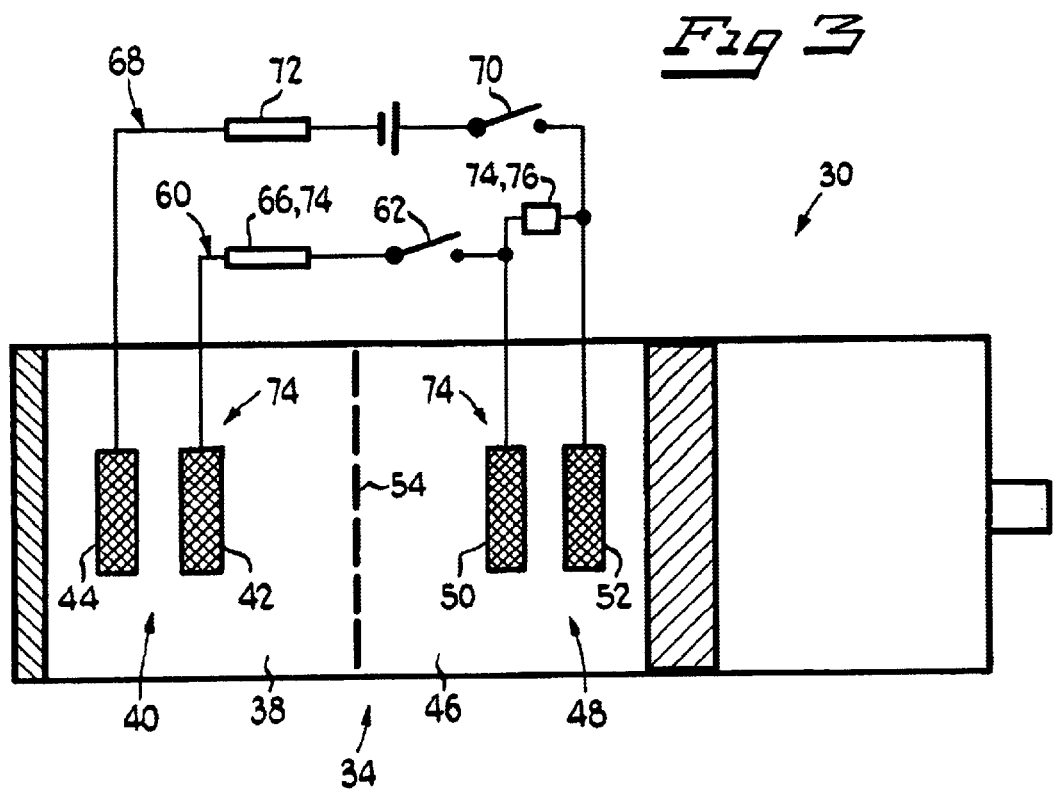
FIG. 3 of the drawings shows a cut-away side view of an alternative embodiment of the fluid delivery device of the present invention.

In another embodiment of the present invention, shown in FIG. 3, first electrode 40 comprises two electrodes, forward first electrode 42 and reverse first electrode 44. Further, it is preferred that second electrode 48 could comprise forward second electrode 50 and reverse second electrode 52. Forward first electrode 42 and forward second electrode 50 can be connected electrically through forward wiring loop 60, and reverse first electrode 44 and reverse second electrode 52 through reverse wiring loop 68. As will be described in the operation section below, such an embodiment allows for a wider selection of electrode materials, as the first electrode 40 and second electrode 46 do not have to be manufactured from electrochemically reversible materials. Although the range of electrode material pairings highlighted above are available for use, in a preferred embodiment of FIG. 3, forward first electrode 42 comprises a zinc electrode, reverse first electrode 44 comprises a platinum electrode, forward second electrode 50 comprises an Ag/AgCl electrode, and reverse second electrode 52 comprises an Ag/AgCl electrode.

Alternatively, and in another preferred embodiment, it may be possible for a single electrode to act as both the forward and reverse electrodes in a single half cell. For example, in the embodiment shown in FIG. 3, there are two separate electrodes within second half cell, namely forward second electrode 50 and reverse second electrode 52. Both the forward and reverse second electrodes could, however, comprise a single second electrode 48 made from electrochemically reversible materials, such as Ag/AgCl. In such an embodiment, forward wiring loop 60 and reverse wiring loop 68 connect forward first electrode 42 and reverse first electrode 44 to a single second electrode. Of course, the entire system could be reversed also, with the first electrode comprising a single electrode, and the second electrode comprising a forward and reverse electrode, as would be known by one of ordinary skill in the art. In any case, a number of different wiring and electrode configurations could provide the present invention with the functionality herein described.

In the embodiment shown in FIG. 3, the sensing means 74 comprises sensing circuits 76 connecting two or more of the electrodes of fluid delivery device 30. In a preferred embodiment, sensing circuit 76 connects forward second electrode 50 and reverse second electrode 52. Alternatively, sensing circuit 76 connects forward first electrode 42 and reverse second electrode 52, forward first electrode 42 and forward second electrode 50, or any other similar combination. Additionally, three or more of the electrodes can be interconnected through sensing means 74. Alternatively, a separate sensing circuit can be inserted into chambers 46 and 38.

In operation, fluid delivery device 30 shown in FIG. 2 is first placed into a fluid-rich environment, such as a human being, so that fluid from the surrounding environment can be absorbed into cell 34 through fluid inlet 32, filling first half-cell 38. Alternatively, the first half-cell 38 could be pre-filled just prior to use or even during manufacture. Once implanted, or just prior to implantation, switch 62 on forward wiring loop 60 is closed, causing the production of ions at the first electrode 40, which ions are then driven across membrane 54 toward and into second half-cell 46. As the ions pass across membrane 54, they take with them small amounts of the water in which they are dissolved, increasing the overall volume of fluid within second half-cell 46.

As volume within the second half-cell 46 is increased, piston 78 is pushed into the sealed compartment 82 of drug reservoir 80, collapsing the volume of that portion inward and towards exit port 84 of fluid delivery device 30. As the sealed compartment 82 is collapsed, it pushes fluid contained therein towards and out of exit port 84, delivering the fluid to the surrounding environment in a consistent and steady manner. Normal operation of the device will continue in the same manner until the first electrode 40 is spent, all fluid is delivered, or an operator makes a decision to halt normal operation of the device.

As normal operation of the device continues, the ionic concentration within the first half-cell 38 and/or second half-cell 46 continues to change. For example, as in one preferred cell 34, namely the Zn/Ag/AgCl embodiment described above, upon closing switch 62, zinc ions are created in the first half cell 38, and sodium ions are then passed across membrane 54 and into second half-cell 46. These ions begin to build up over time, creating an increase in ionic concentration within second half-cell 46, creating an ionic concentration differential between first half cell 38, and second half cell 46. This differential, in part, is the cause for zero-current transport within conventional electro-osmotic cells.

In order to counteract the problem of zero-current transport, an operator of the present invention must counteract the salt concentration increase within the electro-osmotic cell by using zero-current transport control means 58. Control means 58 preferably comprises a combination of wiring apparatus 56, and sensing means 74, which are utilized beneficially together upon halting the operation of the cell. Once a decision has been made to halt the normal operation of the cell 34, sensing means 74 is used to determine the extent of ionic concentration differential between first half-cell 38 and second half-cell 46. In the embodiment of the present invention shown in FIG. 2, sensing circuit 76 detects the ionic concentration differential between the first electrode 40 and the second electrode 46. This information is then transmitted to the control element 72 of the reverse wiring loop 68, where it is evaluated. Control element 72 determines the proper magnitude and time course of current flow necessary to counteract the effects of the ionic concentration differential. Once determined, switch 62 is opened, and switch 70 is closed, and control element 72 directs a reverse flow of current sufficient to counteract the salt concentration increase within the cell, and, in turn, to halt cell 34 operations, and cease the delivery of fluid from fluid delivery device 30 altogether.

Similarly, in the embodiment of the invention shown in FIG. 3, operation of the cell 34 during normal cell operations is commenced by closing switch 62 on forward wiring loop 60, electrically connecting forward first electrode 42 and forward second electrode 50. Once connected, forward first electrode 42 produces an ion within first half-cell 38, which is then transferred across membrane 54, and into second half-cell 46. As with the embodiment discussed above, the transfer of the ions across membrane 54 causes an ionic concentration differential between first half cell 38 and second half cell 46, which in turn causes zero current transport upon the cessation of normal cell operations.

In order to prevent the zero current transport, upon cessation of the normal cell operations, sensing means 74 detects the ionic concentration differential between first half-cell 38 and second half-cell 46. Sensing means 74 uses sensing circuit 76 to detect concentration differences between one of the pairings of forward second electrode 50 and reverse second electrode 52, forward first electrode 42 and reverse first electrode 44, and forward first electrode 42 and forward second electrode 50 (or other electrode combinations). The concentration differences are transferred to control element 72 of reverse wiring loop 68 so that, upon opening switch 62, and closing switch 70, the normal fluid delivery operations of cell 34 can be halted without unwanted zero current transport.

Figure 4:
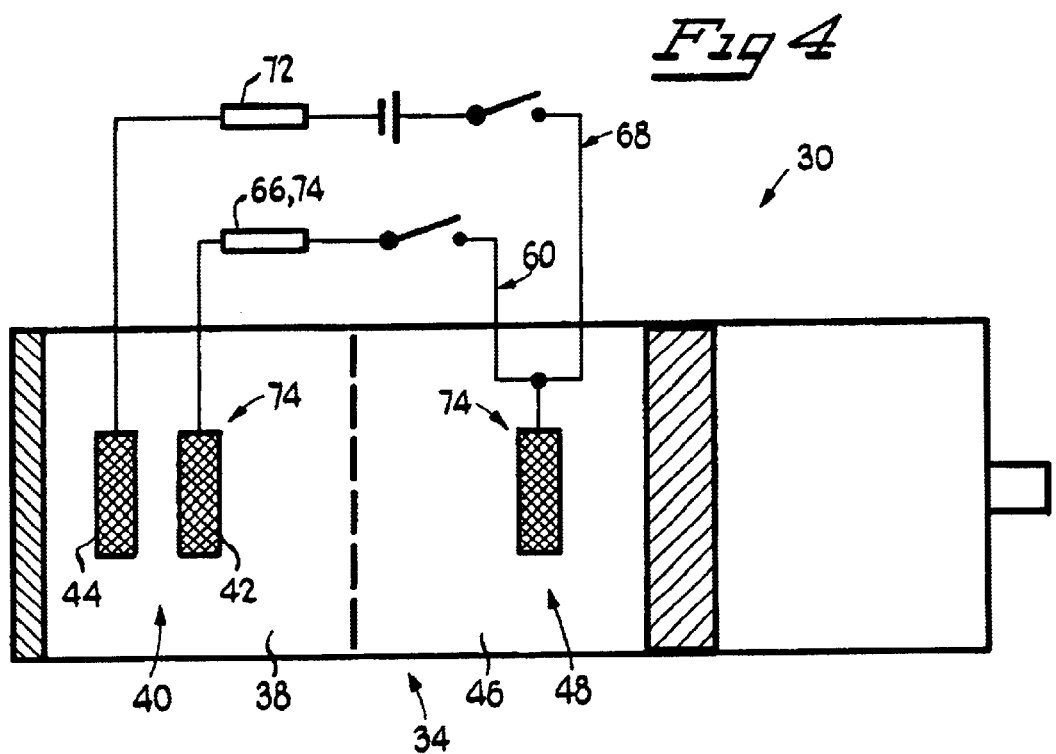
FIG. 4 of the drawings shows an alternative of the fluid delivery device of the present invention.

An alternative embodiment is shown in FIG. 4. In such an embodiment, fluid delivery device 30 includes most of the same elements as embodiments shown in FIGS. 2 and 3, and discussed above. Device 30 includes first half cell 38, and second half-cell 46, with forward wiring loop 60 and reverse wiring loop 68 connecting one or more first electrodes 40, and second electrodes 48. In this embodiment, however, no sensing means 74 is present. The device in FIG. 4 is intended for a single operative session, wherein it is activated once, and then, at the end of its operation, halts function totally. Since the operational life of the device 30 in FIG. 4 is known or limited, control element 72 can implement a known, predetermined current program, reversing the current operation of cell 34 upon cessation of operations. This known current program enables the substantially immediate cessation of fluid delivery from device 30 for the one-time use embodiment shown in FIG. 4.

The foregoing description merely explains and illustrates the invention and the invention is not limited thereto except insofar as the appended claims are so limited, as those skilled in the art that have the disclosure before them will be able to make modifications without departing from the scope of the invention.

What is claimed is:

1. An electro-osmotic cell, comprising:
   a cell housing having a first half cell and a second half cell, with an ion selective membrane therebetween;
   a first electrode positioned within the first half cell;
   a second electrode positioned within the second half cell;
   an electrolyte in electrical communication with the first electrode and the second electrode; and
   a wiring apparatus electrically connecting the first electrode and the second electrode;
   wherein the wiring apparatus comprises means for preventing zero-current transport within the electro-osmotic cell.

2. The electro-osmotic cell according to claim 1, wherein the wiring apparatus comprises a forward wiring loop and a reverse wiring loop, wherein both of the forward wiring loop and the reverse wiring loop comprise a switch associated therewith, such that, upon closing the switch associated with the forward loop, current will flow from the at least one first electrode to the at least one second electrode.

3. The electro-osmotic cell according to claim 2, wherein the preventing means comprises a power source associated with the reverse wiring loop such that, upon closing the switch associated with the reverse wiring loop, current will flow from the at least one second electrode to the at least one first electrode.

4. The electro-osmotic cell according to claim 3, wherein the reverse wiring loop additionally comprises a controlling element for controlling at least one of the magnitude and time course of the current flow across the reverse wiring loop.

5. The electro-osmotic cell according to claim 3, wherein at least one of the at least one first electrode and the at least one second electrode comprises a forward and a reverse electrode.

6. The electro-osmotic cell according to claim 5, wherein both of the at least one first electrode and the at least one second electrode include a forward and a reverse electrode, and the forward first electrode and the forward second electrode are electrically connected through the forward wiring loop, and wherein the reverse first electrode the reverse second electrode are electrically connected through the reverse wiring loop.

7. The electro-osmotic cell according to claim 6, wherein the sensing means comprises a sensing circuit between two or more of the first forward electrode, first reverse electrode, second forward electrode, and second reverse electrode.

8. The electro-osmotic cell according to claim 7, wherein the sensing means comprises a sensing circuit between the forward second electrode and the reverse second electrode.

9. The electro-osmotic cell according to claim 7, wherein the sensing means comprises a sensing circuit between the forward first electrode and the reverse first electrode.

10. The electro-osmotic cell according to claim 7, wherein the sensing means comprises a sensing circuit between the forward first electrode and the forward second electrode.

11. The electro-osmotic cell according to claim 7, wherein the sensing means comprises a sensing circuit between the reverse first electrode and the reverse second electrode.

12. The invention according to claim 1, wherein the electro-osmotic cell additionally comprises means for sensing the concentration of at least one ionic species within at least one of the first half cell and the second half cell.

13. The electro-osmotic cell according to claim 12, wherein the sensing means is capable of detecting the electrical conductivity within at least one of the first half cell and the second half cell, to, in turn, determine the concentration of at least one ionic species.

14. The electro-osmotic cell according to claim 1, wherein the at least one first electrode comprises an anode, and the at least one second electrode comprises a cathode.

15. The electro-osmotic cell according to claim 14, wherein the anode comprises a material selected from the group consisting of carbon, platinum, zinc, magnesium, manganese, aluminum, silver, and silver/silver chloride.

16. The electro-osmotic cell according 14, wherein the cathode comprises a material selected from the group consisting of carbon, platinum, zinc, magnesium, manganese, aluminum, silver, and silver/silver chloride.

17. The electro-osmotic cell according to claim 1, wherein the at least one first electrode comprises cathode, and the at least one second electrode comprises an anode.

18. The invention according to claim 1, wherein the electro-osmotic cell additionally comprises means for sensing the concentration of at least one ionic species within at least one of the first half cell and the second half cell.

19. The electro-osmotic cell according to claim 18, wherein the sensing means is capable of detecting the electrical conductivity within at least one of the first half cell and the second half cell, to, in turn, determine the concentration of at least one ionic species.

20. The electro-osmotic cell according to claim 18, wherein the sensing means comprises a sensing circuit between the at least one first electrode and the at least one second electrode.

21. The electro-osmotic cell according to claim 1, wherein the electrolyte comprises water.

22. The electro-osmotic cell according to claim 1, wherein the electrolyte comprises synthetic solutions that substantially mimic bodily fluids.

23. The electro-osmotic cell according to claim 1, wherein the electrolyte comprises an isotonic saline solution.

24. An electro-osmotic fluid delivery device, comprising:
a fluid inlet;
an electro osmotic cell in fluid communication with the fluid inlet;
a movable barrier adjacent the electro osmotic cell; and
a drug reservoir adjacent the piston member, the drug reservoir comprising a sealed compartment having an exit port;
wherein the electro osmotic cell comprises:
a cell housing having a first half cell and a second half cell, with an ion selective membrane therebetween;
a first electrode positioned within the first half cell;
a second electrode positioned within the second half cell;
an electrolyte in electrical communication with the first electrode and the second electrode; and
a wiring apparatus electrically connecting the at least one first electrode and the at least one second electrode;
wherein the wiring apparatus comprises means for preventing zero-current transport within the electro-osmotic cell.

25. The fluid delivery device according to claim 24, wherein the wiring apparatus comprises a forward wiring loop and a reverse wiring loop, wherein both of the forward wiring loop and the reverse wiring loop comprise a switch associated therewith, such that, upon closing the switch associated with the forward loop, current will flow from the at least one first electrode to the at least one second electrode.

26. The fluid delivery device according to claim 25, wherein the preventing means comprises a power source associated with the reverse wiring loop such that, upon closing the switch associated with the reverse wiring loop, current will flow from the at least one second electrode to the at least one first electrode.

27. The fluid delivery device according to claim 26, wherein the reverse wiring loop additionally comprises a controlling element for controlling at least one of the magnitude and time course of the current flow across the reverse wiring loop.

28. The fluid delivery device according to claim 26, wherein at least one of the at least one first electrode and the at least one second electrode comprises a forward and a reverse electrode.

29. The fluid delivery device according to claim 28, wherein both of the at least one first electrode and the at least one second electrode include a forward and a reverse electrode, and the forward first electrode and the forward second electrode are electrically connected through the forward wiring loop, and wherein the reverse first electrode the reverse second electrode are electrically connected through the reverse wiring loop.

30. The fluid delivery device according to claim 29, wherein the sensing means comprises a sensing circuit between two or more of the first forward electrode, first reverse electrode, second forward electrode, and second reverse electrode.

31. The fluid delivery device according to claim 30, wherein the sensing means comprises a sensing circuit between the forward second electrode and the reverse second electrode.

32. The fluid delivery device according to claim 30, wherein the sensing means comprises a sensing circuit between the forward first electrode and the reverse first electrode.

33. The fluid delivery device according to claim 30, wherein the sensing means comprises a sensing circuit between the forward first electrode and the forward second electrode.

34. The fluid delivery device according to claim 30, wherein the sensing means comprises a sensing circuit between the reverse first electrode and the reverse second electrode.

35. The fluid delivery device according to claim 24, wherein the electro-osmotic cell additionally comprises means for sensing the concentration of at least one ionic species within at least one of the first half cell and the second half cell.

36. The fluid delivery device according to claim 35, wherein the sensing means is capable of detecting the electrical conductivity within at least one of the first half cell and the second half cell, to, in turn, determine the concentration of at least one ionic species.

37. The fluid delivery device according to claim 24, wherein the at least one first electrode comprises an anode, and the at least one second electrode comprises a cathode.

38. The fluid delivery device according to claim 37, wherein the anode comprises a material selected from the group consisting of carbon, platinum, zinc, magnesium, manganese, aluminum, silver, and silver/silver chloride.

39. The fluid delivery device according 37, wherein the cathode comprises a material selected from the group consisting of carbon, platinum, zinc, magnesium, manganese, aluminum, silver, and silver/silver chloride.

40. The fluid delivery device according to claim 24, wherein the at least one first electrode comprises cathode, and the at least one second electrode comprises an anode.

41. The fluid delivery device according to claim 24, wherein the electro-osmotic cell additionally comprises means for sensing the concentration of at least one ionic species within at least one of the first half cell and the second half cell.

42. The fluid delivery device according to claim 41, wherein the sensing means is capable of detecting the electrical conductivity within at least one of the first half cell and the second half cell, to, in turn, determine the concentration of at least one ionic species.

43. The fluid delivery device according to claim 41, wherein the sensing means comprises a sensing circuit between the at least one first electrode and the at least one second electrode.

44. The fluid delivery device according to claim 24, wherein the electrolyte comprises water.

45. The fluid delivery device according to claim 24, wherein the electrolyte comprises synthetic solutions that substantially mimic bodily fluids.

46. The electro-osmotic cell according to claim 24, wherein the electrolyte comprises an isotonic saline solution.

47. The fluid delivery device according to claim 24, wherein the fluid inlet comprises a membrane.

48. The fluid delivery device according to claim 24, wherein the fluid inlet comprises a porous material.

49. The fluid delivery device according to claim 24, wherein the fluid inlet comprises a fluid conduit.

50. The fluid delivery device according to claim 24, wherein the movable barrier comprises a piston.

51. The fluid delivery device according to claim 50, wherein the piston comprises a slideable piston.

52. The fluid delivery device according to claim 24, wherein the movable barrier comprises a flexible diaphragm.

53. The fluid delivery device according to claim 24, wherein the movable barrier comprises a movable partition.

54. A single-use electro-osmotic fluid delivery device, comprising:
 a fluid inlet;
 an electro osmotic cell in fluid communication with the fluid inlet;
 a movable barrier adjacent the electro osmotic cell; and
 a drug reservoir adjacent the piston member, the drug reservoir comprising a sealed compartment having an exit port;
 wherein the electro osmotic cell comprises:
  a cell housing having a first half cell and a second half cell, with an ion selective membrane therebetween;
  a first electrode positioned within the first half cell;
  a second electrode positioned within the second half cell;
  an electrolyte in electrical communication with the first electrode and the second electrode; and
  a wiring apparatus electrically connecting the at least one first electrode and the at least one second electrode;
  wherein the wiring apparatus comprises means for reversing the current between the first electrode and second electrode at a predetermined magnitude for a predetermined period of time after cessation of cell operations.

55. A method for controlling unwanted fluid flow in an electro osmotic fluid delivery device, comprising the steps of:
 delivering a fluid using an electro-osmotic fluid delivery device having an electro-osmotic cell therein, wherein the step of delivering comprises the step of increasing a salt concentration within the electro-osmotic cell;
 sensing the salt concentration within the electro-osmotic cell;
 halting the step of delivering; and
 preventing zero-current transport due to the increased salt concentration by reversing the direction of current proportionally to the sensed salt concentration, and, in turn, substantially reducing unwanted fluid delivery out of the fluid delivery device.

56. The method according to claim 55, wherein the step of sensing the salt concentration comprises sensing the conductivity differences between at least two of a forward first electrode, a forward second electrode, a reverse first electrode and a reverse second electrode, wherein the forward and reverse first electrodes are located within a first half cell of the electro-osmotic cell, and the forward and reverse second electrodes are located within a second half cell of the electro-osmotic cell.

57. A method for controlling unwanted fluid flow in a single-use electro osmotic fluid delivery device, comprising the steps of:
 delivering a predetermined amount of fluid using an electro-osmotic fluid delivery device having an electro-osmotic cell therein, wherein the step of delivering comprises the step of increasing a salt concentration within the electro-osmotic cell to a substantially predetermined level;
 halting the step of delivering; and
 preventing zero-current transport due to the increased salt concentration by reversing the direction of current at a predetermined magnitude for a predetermined period of time, and, in turn, substantially reducing unwanted fluid delivery out of the fluid delivery device.

* * * * *